United States Patent [19]
Hein

[11] Patent Number: 5,632,728
[45] Date of Patent: May 27, 1997

[54] SKIN TESTING AND VACCINATING NEEDLES

[75] Inventor: Gary L. Hein, Oakley, Ill.

[73] Assignee: Lincoln Diagnostics, Inc., Decatur, Ill.

[21] Appl. No.: 345,221

[22] Filed: Nov. 28, 1994

Related U.S. Application Data

[63] Continuation-in-part of Ser. No. 199,099, Feb. 22, 1994, abandoned.

[51] Int. Cl.$^6$ .................................................. A61B 17/20
[52] U.S. Cl. .................... 604/46; 604/22; 604/310
[58] Field of Search ........................... 604/22, 46, 47, 604/272–274, 310, 311, 240

[56] References Cited

U.S. PATENT DOCUMENTS

| | | |
|---|---|---|
| 2,512,568 | 8/1950 | Saffir . |
| 2,512,569 | 6/1950 | Saffir . |
| 3,119,391 | 1/1964 | Harrison . |
| 3,194,237 | 7/1965 | Rubin . |
| 3,512,520 | 5/1970 | Cowan .................... 128/743 |
| 3,905,371 | 9/1975 | Stickl et al. . |
| 3,948,261 | 4/1976 | Steiner . |
| 4,712,548 | 12/1987 | Enstrom . |
| 4,838,877 | 6/1989 | Massau .................... 604/172 |
| 4,869,259 | 9/1989 | Elkins .................... 604/272 |
| 5,104,620 | 4/1992 | Wiley et al. .................... 422/61 |
| 5,250,066 | 10/1993 | Lambert .................... 606/181 |

FOREIGN PATENT DOCUMENTS

| | | | |
|---|---|---|---|
| 840896 | 6/1952 | Germany | 604/272 |
| 0271511 | 7/1964 | Netherlands | 604/272 |

Primary Examiner—Robert A. Clarke
Attorney, Agent, or Firm—Lockwood, Alex, Fitzgibbon & Cummings

[57] ABSTRACT

A plastic skin testing and vaccinating needle characterized by an end bifurcated into two sharp points spaced sufficiently close so that the points will form a small hole in the skin when the needle is simultaneously rotated and pressed against the skin. The spacing also causes liquid to adhere to and between the points when the end is dipped in skin testing or vaccinating liquid. The cross-section of the needle shaft is sufficiently large that the needle can be readily rotated between a user's thumb and index finger. Rotation is facilitated by altering or roughening the surface of the shaft so as to reduce slippage during rotation. Preferably, the needle is formed in a die produced by electro-discharge machining so as to have an etched or matte surface which enhances the adherence of liquid to the bifurcated end.

12 Claims, 1 Drawing Sheet

FIG. 1
FIG. 2
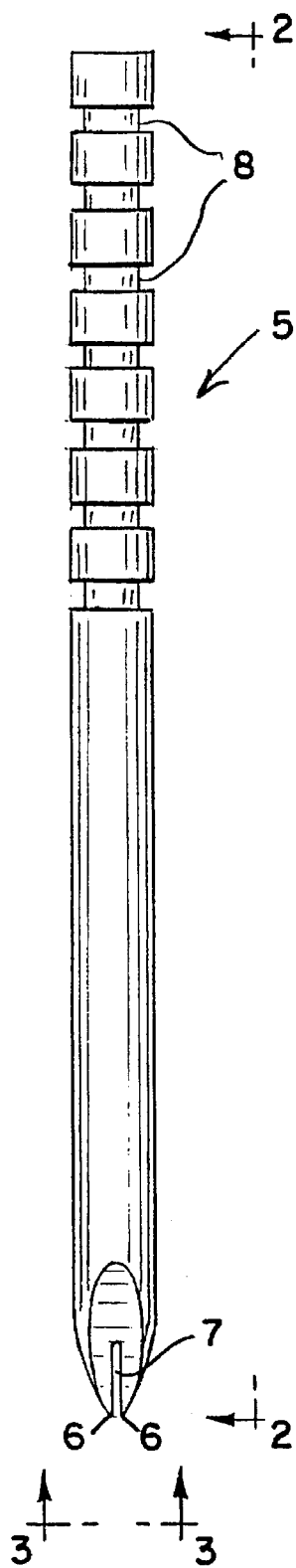
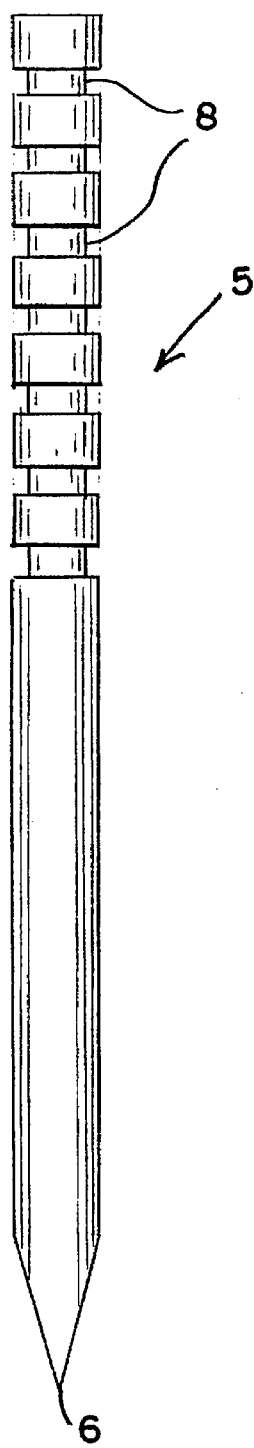
FIG. 3
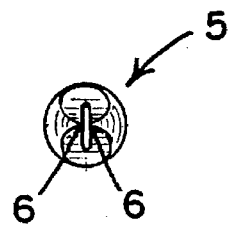

SKIN TESTING AND VACCINATING NEEDLES

This application is a continuation-in-part of application Ser. No. 08/199,099, filed Feb. 22, 1994 now abandoned.

BACKGROUND OF THE INVENTION

This invention relates, generally, to innovations and improvements in needles used for skin testing or vaccinating which are formed of plastic and have a bifurcated end providing two sharp points for engaging the skin of a subject to be tested or vaccinated. The invention also relates to new and improved methods of skin testing and vaccinating using such needles.

DESCRIPTION OF RELATED ART

Various types of needles are disclosed in the prior art for use in conducting skin tests for allergies and for conducting vaccinations or inoculations. While it has been suggested in certain prior art that some needles can be formed of plastic materials, commercially, bifurcated needles have been formed from small diameter (e.g., 0.03 inch) steel wire stock from which the needles are stamped so as to be bifurcated and flattened at one end to provide two sharp points which are used to prick or puncture the skin. A stamping out tool loses its cutting edge during the manufacturing process and as a result the bifurcated ends become less refined in respect to sharpness and uniform length of points. While stamping out tools can be changed at periodic intervals, it is impossible to maintain the same degree of precision for the bifurcated points as the stamping out tool nears the end of its useful life. Such steel needles have been used in primarily two different ways. According to one way, the needles are used to produce a perpendicular puncture of the skin. According to the second way, they are used to conduct what is referred to as a "modified prick test" wherein the shaft of the needle is held at an angle of about 45° to the plane of the skin and then the skin is lifted slightly by one of the points through a drop of test material. Since the shafts of these needles are quite slender and smooth, they do not lend themselves to being used according to a third and highly desirable technique provided by the present invention wherein the needles are rotated between the user's thumb and index finger while the points are simultaneously pressed against the skin so as to drill a small hole which penetrates the epidermis.

SUMMARY OF THE INVENTION

According to the present invention, skin testing and vaccinating needles are formed of plastic and the needle shafts, when round, are approximately 0.1 inch in diameter. By forming the needles of the invention with cross sections of approximately 0.1 inch diameter, they lend themselves to being readily rotated between the user's thumb and index finger, without slippage, so that the points at the bifurcated end have a drilling action when pressed against the skin so as to achieve epidermal penetration and form a small hole in the skin rather than only superficially scratching or abrading the skin. However, in order to drill such small holes in the skin, the sharp points must be sufficiently close together so as to produce the hole forming or drilling action. Otherwise, if the points are too widely spaced, or not accurately formed, they will not form the desired small holes.

It is not possible to stamp out from wire stock needles which have shafts with diameters in the order of 0.1 inch and small bifurcated ends with sharp points spaced close enough to drill small holes in the skin by rotating the needles. Furthermore, when the needles are stamped out of steel as in the prior art the metal is flattened at the bifurcated ends so that the flattened juncture between the round shafts and the points are hip-like in shape and appreciably wider than the diameter of the shafts. These hip-like junctures cause these prior steel needles to pick up extra amounts of test substance with each dipping which is wasted. By molding the needles from plastic in accordance with this invention the shafts can be as large as desired, the bifurcated end as small as desired, the sharp points can be as closely spaced as desired, and the hip-like junctures can be eliminated.

In order to facilitate the rotation of the needle which produces the hole drilling action, it is preferred that in addition to the shaft of the needle having a large enough cross sectional dimension, slippage between the thumb and index finger be eliminated or reduced by suitably altering or augmenting the surface of the needle shaft such as by notching, knurling or otherwise altering or mutilating the surface, at least where it is engaged by the user's thumb and index finger. When the sharp points are spaced properly for imparting the hole drilling function to the points, the spacing will also be such as to enhance the ability of the needle to pick up and retain on the bifurcated end a small but suitable amount of testing or vaccinating liquid when the needle is dipped into and withdrawn from a body of such a liquid. This ability and property can be enhanced by providing at least the bifurcated end of the needle with an etched or matte finish. Such a finish can be provided by using forming molds which have been produced by electro-discharge machining.

In view of the foregoing, the object of the invention, generally stated, is the provision of skin testing and vaccinating needles and method of use thereof characterized by: being formed of plastic; having a large enough shaft diameter or cross section so as to be easily rotated between the thumb and index finger of the user; being bifurcated at one end and being so small as to provide two sharp points which are accurately formed and precisely spaced close enough together so that they will have a hole drilling capability when a needle is simultaneously rotated and pressed into the skin so as to penetrate into and form a small hole therein; the bifurcated end having an etched or matte finish to improve the pick-up and adherence thereto of medicament; and the portion of the needle shaft that is engaged by the thumb and index finger to produce rotation being roughened or so shaped so as to reduce slippage between the needle and the thumb and index finger of the user during rotation.

Certain other important objects of the invention will be obvious to those skilled in the art, particularly, when the invention is viewed in light of the following detailed description thereof taken with the accompanying drawings wherein:

BRIEF DESCRIPTION OF THE DRAWINGS

FIG. 1 is a side elevational view on enlarged scale of a skin testing and vaccinating needle forming one embodiment of the invention;

FIG. 2 is a side elevational view of the needle shown in FIG. 1 but taken at a right angle to FIG. 1; and FIG. 3 is a bottom end view of the bifurcated end of the needle shown in FIGS. 1 and 2.

DESCRIPTION OF THE PREFERRED EMBODIMENT

Referring to the drawings, a skin testing and vaccinating needle is indicated generally at 5 which from the standpoints of quality of its sharp points and cost is injection molded from a suitable plastic material, preferably in molds the molding surfaces of which have been formed by electro-discharge machining techniques. The needle 5 may be formed from several different commercial plastics including acrylics and styrenes.

As viewed in FIGS. 1 and 2, the bottom end of the needle 5 is bifurcated so as to have two sharp points 6—6 of identical shape and length. The width of the space 7 between the sharp points 6 is critical in order that these points will, in effect, drill a very small hole in the skin when the needle 5 is rotated and the point 6 pressed into the skin. It has been found that the space 7 should be approximately 0.015 of an inch in width since an appreciably wider spacing will not allow the points to have a hole drilling action. On the other hand, it is desirable that the space 7 not be too small since the proper spacing of the points 6 also serves to improve the ability of the bifurcated end to pick-up and retain thereon liquid skin testing and vaccinating reagents.

The needle 5 may be formed by known techniques, preferably, by injection molding in molds produced by electro-discharge machining. Such molds will inherently impart an etched or matte-like finish to the surface of the needle. This surface enhances the ability of the bifurcated end to pick-up and hold adequate amounts of skin testing or vaccinating reagents and also imparts a roughening effect to the upper end of the needle shaft which tends to reduce slippage between the user's thumb and forefinger. This slippage can also be materially reduced by providing the needle with a plurality of circumferential notches 8. Instead of using notches 8, the same portion of the needle 5 can be knurled. In both cases, the notches 8 or the knurling can be provided by suitably machining the forming molds. Also, the handle portions of the needles may have hexagonal or other flat-sided cross-sections.

What is claimed is:

1. A plastic skin testing and vaccinating needle consisting of a straight shaft at least one end of which is bifurcated into two sharp points spaced so as to both pick up by dipping and retention thereon and therebetween a desired quantity of skin testing or vaccinating liquid and upon simultaneous rotation and pressing drill a small hole in the skin so as to achieve epidermal penetration, at least a portion of said shaft having a length and a cross-sectional shape and being large enough in size to facilitate rotation of the needle about its longitudinal axis by rotation between a user's finger and thumb.

2. The skin testing and vaccinating needle of claim 1, wherein the surface of said portion of the length rotatable between the user's thumb and finger is altered so as to reduce slippage between said portion and the user's thumb and finger.

3. The skin testing and vaccinating needle of claim 2, wherein said surface is altered by rendering it non-smooth to the touch.

4. A skin testing and vaccinating needle formed of plastic and consisting of a straight shaft at least one end of which is bifurcated into two sharp points spaced to pick up by dipping and retain thereon and therebetween a desired quantity of skin testing or vaccinating liquid, at least a portion of said shaft having a length and a cross-sectional shape and large enough in size to facilitate rotation of the needle about its longitudinal axis by rotation between a user's finger and thumb, and said spacing of said two sharp points also being sufficiently close together so that said sharp points will form a small hole in the skin upon said rotation of said needle combined with pressure against the skin.

5. The skin testing and vaccinating needle of claim 4, wherein the spacing of said sharp points does not exceed about 0.015 of an inch between their distal ends.

6. A skin testing and vaccinating needle formed of plastic and consisting of a straight shaft at least one end of which is bifurcated into two sharp points spaced to pick up by dipping and retain thereon and therebetween a desired quantity of skin testing or vaccinating liquid, at least a portion of said shaft having a length and a cross-sectional shape and large enough in size to facilitate rotation of the needle about its longitudinal axis by rotation between a user's finger and thumb, and said spacing of said two sharp points also being sufficiently close together so that said sharp points will form a small hole in the skin upon said rotation of said needle combined with pressure against the skin, and wherein said small hole penetrates approximately to the full depth of the epidermal layer.

7. A skin testing and vaccinating needle formed of plastic and consisting of a straight shaft at least one end of which is bifurcated into two sharp points spaced to pick up by dipping and retain thereon and therebetween a desired quantity of skin testing or vaccinating liquid, at least a portion of said shaft having a length and a cross-sectional shape and large enough in size to facilitate rotation of the needle about its longitudinal axis by rotation between a user's finger and thumb, and said spacing of said two sharp points also being sufficiently close together so that said sharp points will form a small hole in the skin upon said rotation of said needle combined with pressure against the skin, wherein the spacing of said sharp points at their distal ends is approximately 0.015 of an inch.

8. A plastic skin testing and vaccinating needle consisting of a straight shaft at least one end of which is bifurcated into two sharp points spaced so as to both pick up by dipping and retention thereon and therebetween a desired quantity of skin testing or vaccinating liquid and upon simultaneous rotation and pressing drill a small hole in the skin so as to achieve epidermal penetration, at least a portion of said shaft having a length and a cross-sectional shape and being large enough in size to facilitate rotation of the needle about its longitudinal axis by rotation between a user's finger and thumb, wherein the surface thereof at least at the end including said sharp points thereat is an etched or matted surface which enhances the adherence thereto of skin testing or vaccinating liquid.

9. A method of skin testing or vaccinating with a skin testing or vaccinating needle having a dual pointed end which comprises simultaneously rotating the needle between a thumb and finger and pressing into the skin its dual pointed end loaded with an antigen or vaccine so as to drill a small hole into the skin sufficiently deep to achieve epidermal penetration and thereby deposit the antigen or vaccine at a site beneath the surface of the skin.

10. The method of claim 9, wherein said needle is formed of plastic and comprises a straight shaft at least one end of which is bifurcated into sharp points spaced so as to pick up and return thereon and therebetween a desired load of skin testing or vaccinating liquid, at least a portion of said shaft having a length and cross-sectional shape and size large enough to facilitate rotation of the needle about its longitudinal axis by rotation between a user's thumb and finer.

11. The method of claim 10, wherein the spacing of said sharp points at their distal ends does not exceed approximately 0.015 of an inch.

12. The method of claim 9 wherein said site of deposit is into the epidermal layer to a depth approximately reaching the dermis.

* * * * *